United States Patent [19]

Cantello

[11] 4,333,929
[45] Jun. 8, 1982

[54] CARBOXAMIDINE DERIVATIVES AND HYPOGLYCEMICAL USE

[75] Inventor: Barrie C. C. Cantello, Redhill, England

[73] Assignee: Beecham Group Limited, England

[21] Appl. No.: 226,180

[22] Filed: Jan. 19, 1981

[30] Foreign Application Priority Data

Jan. 22, 1980 [GB] United Kingdom ............... 8002132

[51] Int. Cl.³ .................. A61K 31/155; A61K 31/54; C07C 129/00; C07D 279/10
[52] U.S. Cl. ................................. 424/246; 564/238; 564/239; 424/248.4; 564/240; 548/532; 424/248.58; 424/250; 424/251; 424/267; 424/270; 424/272; 424/273 R; 424/274; 424/326; 544/3; 544/53; 544/59; 544/63; 544/88; 544/162; 544/165; 544/224; 544/242; 544/335; 544/402; 546/231; 546/246; 548/146; 548/214; 548/215; 548/240; 548/300; 548/356; 548/569; 548/531
[58] Field of Search ............... 260/326.5 L, 326.86; 544/3, 53, 59, 63, 88, 162, 165, 224, 242, 335, 402; 546/231, 246; 548/146, 214, 215, 240, 300, 356; 424/246, 248.4, 248.58, 250, 251, 267, 270, 272, 273 R, 274, 326; 564/238, 239, 240

[56] References Cited

U.S. PATENT DOCUMENTS 3,261,809 7/1966 Sherr ........................... 564/240 X

FOREIGN PATENT DOCUMENTS 952 4/1979 European Pat. Off. .
1409768 6/1975 United Kingdom .

OTHER PUBLICATIONS

Chem. Abst., 89, (Dec. 4, 1978), p. 51, No. 19105m.

Primary Examiner—Richard Raymond
Attorney, Agent, or Firm—Jacobs & Jacobs

[57] ABSTRACT

A compound of formula (II) or a pharmaceutically acceptable acid addition salt thereof

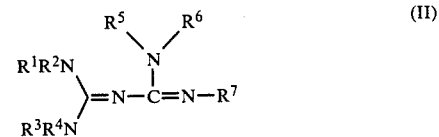

wherein $R^1$, $R^2$, $R^3$ and $R^4$ are the same or different and each represents $C_{1-6}$ alkyl; $R^5$ represents hydrogen or $C_{1-6}$ alkyl; $R^6$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^5$ and $R^6$ together represent the remaining members of a 5- or 6-membered ring optionally containing an oxygen, sulphur or additional nitrogen atom and being optionally substituted with $C_{1-6}$ alkyl, carboxy or $C_{1-6}$ alkoxycarbonyl; and $R^7$ represents $C_{1-6}$ alkyl, phenyl optionally substituted with up to 3 groups selected from halogen, $C_{1-6}$ alkyl and $C_{1-6}$ alkoxy; or benzyl optionally substituted with up to 3 groups selected from halogen, $C_{1-6}$ alkyl and $C_{1-6}$ alkoxy, has useful hypoglycaemic activity.

13 Claims, No Drawings

CARBOXAMIDINE DERIVATIVES AND HYPOGLYCEMICAL USE

This invention relates to a class of novel carboxamidine derivatives which are useful in the treatment of diabetes. The invention also relates to a process for their preparation and to pharmaceutical compositions containing them.

The compound of formula (I):

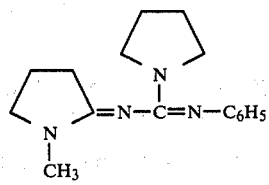

has been reported to be useful in the treatment of diabetes in Belgian Pat. No. 852,565 and in Diabetes, 27, 856 and 868 (1978).

We have now found a class of carboxamidine derivatives which have hypoglycaemic activity.

Accordingly, the present invention provides a compound of formula (II) or a pharmaceutically acceptable acid addition salt thereof:

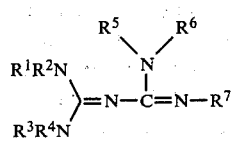

wherein $R^1$, $R^2$, $R^3$ and $R^4$ are the same or different and each represents $C_{1-6}$ alkyl; $R^5$ represents hydrogen or $C_{1-6}$ alkyl; $R^6$ represents $C_{1-6}$ alkyl, phenyl optionally substituted with up to 3 groups selected from halogen, $C_{1-6}$ alkyl, and $C_{1-6}$ alkoxy; or benzyl optionally substituted with up to 3 groups selected from halogen, $C_{1-6}$ alkyl and $C_{1-6}$ alkoxy; or $R^5$ and $R^6$ together represent the remaining members of a 5- or 6-membered ring optionally containing an oxygen, sulphur or additional nitrogen atom and being optionally substituted with $C_{1-6}$ alkyl, carboxy or $C_{1-6}$ alkoxycarbonyl; and $R^7$ represents $C_{1-6}$ alkyl, phenyl, optionally substituted with up to 3 groups selected from halogen, $C_{1-6}$ alkyl and $C_{1-6}$ alkoxy; or benzyl optionally substituted with up to 3 groups selected from halogen, $C_{1-6}$ alkyl and $C_{1-6}$ alkoxy.

Suitable acid addition salts of compound (II) include inorganic salts such as the sulphate, nitrate, phosphate, and borate, hydrohalides such as the hydrochloride, hydrobromide and hydroiodide, and organic acid addition salts such as acetate, oxalate, tartrate, maleate citrate, succinate, benzoate, ascorbate, methanesulphonate and p-toluene-sulphonate.

Preferred salts are hydrohalide salts.

Examples of suitable $C_{1-6}$ alkyl groups which $R^1$ to $R^6$ may represent include methyl, ethyl, n- and iso-propyl, and n-, sec-, iso- and tert-butyl.

Suitable substituents for the phenyl and benzyl groups for $R^6$ and the phenyl group for $R^7$ include ortho-, meta- and para-methyl, methoxy, chloro and bromo.

Preferably, $R^1$, $R^2$, $R^3$ and $R^4$ each represents methyl.

Suitably $R^5$ is hydrogen, methyl, ethyl or n-propyl, and $R^6$ represents methyl, ethyl, n-propyl, phenyl or benzyl. When $R^5$ and $R^6$ complete a ring, suitably such rings include pyrrolidine, piperidine, morpholine, thiomorpholine, piperazine and 4-($C_{1-6}$ alkyl) piperazine, for example 4-methylpiperazine rings.

Preferably, $R^5$ and $R^6$ each represents ethyl.

Suitably $R^7$ is phenyl.

Preferred compounds of formula (II) are the following:

N-(Bis[Dimethylamino]methylene)-N'-phenyl-4-morpholine carboxamidine

N-(Bis[Dimethylamino]methylene)-N'-phenyl-1-pyrrolidine carboxamidine

N'-(Bis[Dimethylamino]methylene)-N,N-diethyl-N''-phenyl guanidine.

Compounds of formula (II) may be prepared by reacting a compound of formula (III):

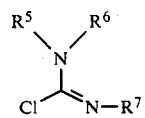

wherein $R^5$, $R^6$ and $R^7$ are as defined with respect to formula (II) above; with an imino compound (IV)

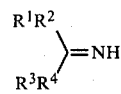

where $R^1$, $R^2$, $R^3$ and $R^4$ are as defined with respect to formula (II) above, and thereafter, where desired, converting a free base of formula (II) so obtained into a pharmaceutically acceptable salt or converting a salt of a compound of formula (II) so obtained into the free base.

The reaction is conveniently carried out in a nonhydroxylic solvent system such as an ether, chlorinated hydrocarbon or a mixture thereof. Suitable solvent systems include mixtures of diethyl ether and chloroform. The reaction is suitably carried out at ambient temperature. The period for which the reaction is allowed to proceed depends upon the starting materials employed. The course of the reaction may be followed by conventional methods such as thin layer chromatography, and terminated when an optimum quantity of product is present in the reaction mixture. However, in general, we have found it convenient to leave the reaction mixture to stand overnight.

The intermediates of formula (III) may be prepared by reaction of an isocyanide dichloride of formula: $R^7—N=CCl_2$ wherein $R^7$ is as defined with respect to formula (II) above with an amine of formula $R^5R^6NH$, wherein $R^5$ and $R^6$ are as defined with reference to formula (II) above. Suitably the reaction is carried out in ethereal solvent such as diethyl ether or tetrahydrofuran. The reaction is suitably carried out at ambient temperature. The period for which the reaction is allowed to proceed may be determined by methods as described hereinbefore; however we have found a one- to two-hour reaction time to be sufficient.

In order to put the compounds (II) to use as medicinal agents for the treatment of diabetes, they are presented as pharmaceutical compositions in a variety of dosage forms. This invention therefore also includes a pharmaceutical composition which comprises a compound of formula (II) together with a pharmaceutically acceptable carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example acacia, gelatin, sorbitol, tragacanth, or polyvinylpyrolidone; fillers, for example calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxy-benzoate or sorbic acid, and if desired conventional flavouring or colouring agents. The compounds may also if desired be incorporated in a foodstuff, for example in the form of a biscuit.

Suppositories will contain conventional suppository bases, e.g. cocoa butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic preservative and buffering agents can be dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10 to 60% by weight, of the active material, depending on the method of administration. The dosage employed for adult treatment will, of course, depend on the dose-response characteristics of the particular active ingredient but will normally be in the range 0.5 to 150 mg/kg/day.

The following Examples illustrate the preparation of a number of compounds of this invention.

EXAMPLE 1

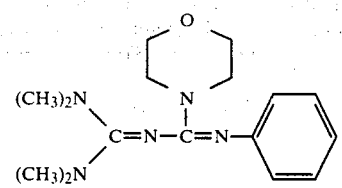

N-(BIS[DIMETHYLAMINO]METHYLENE)-N'-PHENYL-4-MORPHOLINE CARBOXAMIDINE

Morpholine (5.56 g) in dry diethyl ether (50 ml) was added dropwise to a stirred solution of phenylisocyanide dichloride (5.55 g) in dry diethyl ether (50 ml) at 0° C. over 15 minutes and the resultant mixture stirred for one hour and filtered. To this filtrate, 1,1,3,3,-tetramethylguanidine (6.51 g) in dry ether (40 ml) was added and the mixture stirred for 18 hours, filtered and the filtrate evaporated to dryness. The residue was dissolved in dilute hydrochloric acid, washed with ether, basified with aqueous sodium hydroxide solution and extracted with ether. The ethereal extract was washed with water, dried over anhydrous magnesium sulphate, filtered and evaporated to dryness to give a solid. Recrystallisation from petroleum ether, bp 80°-100° C., gave analytically pure product, mpt 115°-119° C.

EXAMPLES 2 AND 3

By an analogous procedure to that described in Example 1, the following compounds were prepared:

EXAMPLE 2

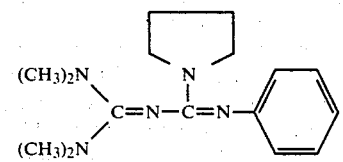

N-(BIS[DIMETHYLAMINO]METHYLENE)-N'-PHENYL-1-PYRROLIDINE CARBOXAMIDINE mpt 128°-130° C. (petroleum ether, bp 80°-100° C.)

EXAMPLE 3

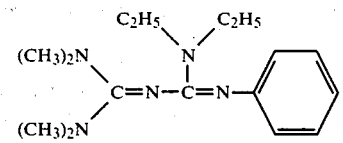

N'-(BIS[DIMETHYLAMINO]METHYLENE)-N,N-DIETHYL-N''-PHENYL GUANIDINE mpt 50°-51.5° C.

BIOLOGICAL DATA

Activity on Glucose Tolerance in Fasted Mice

For this assay mice were fasted for 24 hours before the experiment and then randomised so that each treatment group contained 8 mice. The compounds were dosed orally in 1% aqueous carboxymethyl cellulose (10 ml/kg body weight), and 30 minutes later glucose (1 g/kg) was administered by the sub-cutaneous route. Blood samples for glucose analysis were taken from the tail 60 minutes after glucose administration; the results are shown in the table below.

TABLE

| Compound of Example No. | Dose mmol/kg | Blood Glucose concentration mmol/liter 60 minutes after subcutaneous glucose |
|---|---|---|
| 1 | 0 | 6.67 |
|   | 0.2 | 4.35 |
| 2 | 0 | 7.46 |
|   | 0.2 | 6.56 |
| 3 | 0 | 8.45 |
|   | 0.2 | 5.54 |

I claim:

1. A compound of the formula:

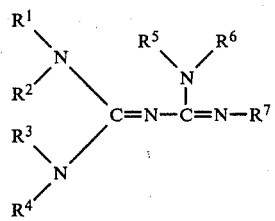

or a pharmaceutically acceptable acid addition salt thereof wherein
  each of $R^1$, $R^2$, $R^3$ and $R^4$ independently of the others is alkyl of 1 to 6 carbon atoms;
  $R^5$ when taken independently of $R^6$ is hydrogen or alkyl of 1 to 6 carbon atoms;
  $R^6$, when taken independently of $R^5$ is alkyl of 1 to 6 carbon atoms, phenyl or benzyl, said phenyl and benzyl being unsubstituted or substituted with from 1 to 3 members selected from the group consisting of halo, alkyl of 1 to 6 carbon atoms and alkoxy of 1 to 6 carbon atoms; or
  $R^5$ and $R^6$ together with the nitrogen to which they are attached are a 5 to 6 membered heterocyclic ring containing said nitrogen as the sole hetero atom or containing a member selected from the group consisting of nitrogen, oxygen or sulfur as a second hetero atom; and
  $R^7$ phenyl or benzyl, said phenyl and benzyl being unsubstituted or substituted with from 1 to 3 members selected from the group consisting of halo, alkyl of 1 to 6 carbon atoms and alkoxy of 1 to 6 carbon atoms.

2. A compound according to claim 1 wherein each of $R^1$, $R^2$, $R^3$ and $R^4$ is methyl, ethyl, n-propyl, iso-propyl, n-butyl, sec-butyl, iso-butyl or tert-butyl.

3. A compound according to claim 2 wherein each of $R^1$, $R^2$, $R^3$ and $R^4$ is methyl.

4. A compound according to claim 1 wherein $R_5$ is hydrogen, methyl, ethyl or n-propyl and $R_6$ is methyl, ethyl, ethyl, n-propyl, phenyl or benzyl.

5. A compound according to claim 1 wherein $R_5$ and $R_6$ together with the nitrogen atom to which they are attached are pyrrolidino, piperidino, morpholino, thiamorpholino, piperazino, or 4-alkylpiperazino wherein alkyl contains 1 to 6 carbon atoms.

6. A compound according to claim 1 wherein $R_7$ is phenyl.

7. A pharmaceutical composition which comprises a hypoglycemically effective amount of a compound according to claim 1 in combination with a pharmaceutically acceptable carrier.

8. The method of effecting a hypoglycemic response in an animal in need thereof which comprises administering thereto an effective amount of a compound of the formula:

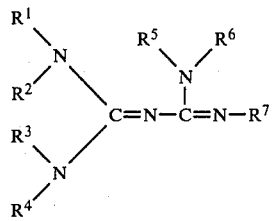

or a pharmaceutically acceptable acid addition salt thereof wherein
  each of $R^1$, $R^2$, $R^3$ and $R^4$ independently of the others is alkyl of 1 to 6 carbon atoms;
  $R^5$ when taken independently of $R^6$ is hydrogen or alkyl of 1 to 6 carbon atoms;
  $R^6$, when taken independently of $R^5$ is alkyl of 1 to 6 carbon atoms, phenyl or benzyl, said phenyl and benzyl being unsubstituted or substituted with from 1 to 3 members selected from the group consisting of halo, alkyl of 1 to 6 carbon atoms and alkoxy of 1 to 6 carbon atoms; or
  $R^5$ and $R^6$ together with the nitrogen to which they are attached are a 5 to 6 membered heterocyclic ring containing said nitrogen as the sole hetero atom or containing a member selected from the group consisting of nitrogen, oxygen or sulfur as a second hetero atom; and
  $R^7$ is alkyl of 1 to 6 carbon atoms, phenyl or benzyl, said phenyl and benzyl being unsubstituted or substituted with from 1 to 3 members selected from the group consisting of halo, alkyl of 1 to 6 carbon atoms and alkoxy of 1 to 6 carbon atoms.

9. The method according to claim 8, wherein each of $R^1$, $R^2$, $R^3$ and $R^4$ is methyl, ethyl, n-propyl, iso-propyl, n-butyl, sec-butyl, iso-butyl or tert-butyl.

10. The method according to claim 9, wherein each of $R^1$, $R^2$, $R^3$ and $R^4$ is methyl.

11. The method according to claim 8, wherein $R_5$ is hydrogen, methyl, ethyl or n-propyl and $R_6$ is methyl, ethyl, n-propyl, phenyl or benzyl.

12. The method according to claim 8, wherein $R_5$ and $R_6$ together with the nitrogen atom to which they are attached are pyrrolidino, piperidino, morpholino, thiamorpholino, piperazino, or 4-alkylpiperazino wherein alkyl contains 1 to 6 carbon atoms.

13. The method according to claim 8, wherein $R_7$ is phenyl.

* * * * *